(12) United States Patent
Nowotny et al.

(10) Patent No.: US 6,723,346 B1
(45) Date of Patent: Apr. 20, 2004

(54) PROCESS FOR PREPARING SPRAY GRANULES CONTAINING RIBOFLAVIN

(75) Inventors: Markus Nowotny, Rheinfelden (CH); Jean-Claude Tritsch, Saint-Louis (FR)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/550,971

(22) Filed: Apr. 17, 2000

(30) Foreign Application Priority Data

Apr. 30, 1999 (EP) ............................. 99108476

(51) Int. Cl.⁷ ............... A61K 9/14; A61K 9/20; A61K 9/26; B05D 7/00
(52) U.S. Cl. .............. 424/489; 424/464; 424/465; 424/470; 427/213
(58) Field of Search ............... 424/489, 464, 424/465, 470; 427/213

(56) References Cited

U.S. PATENT DOCUMENTS

| | | | |
|---|---|---|---|
| 4,977,190 A | * 12/1990 | Meyer et al. | ............... 514/951 |
| 5,137,732 A | 8/1992 | Buehler et al. | |
| 5,236,920 A | * 8/1993 | Kilbride, Jr. et al. | ....... 514/251 |
| 5,300,303 A | * 4/1994 | Grimmer et al. | ........... 424/489 |
| 6,093,715 A | * 7/2000 | Harz et al. | .................. 514/251 |

FOREIGN PATENT DOCUMENTS

| | | |
|---|---|---|
| EP | 0 414 115 B1 | 3/1993 |
| EP | 0 457 075 B1 | 2/1996 |
| EP | 0 995 749 A1 | 4/2000 |

OTHER PUBLICATIONS

Derwent English language abstract of EP 0 995 749 A1 (Document B3).

* cited by examiner

Primary Examiner—Thurman K. Page
Assistant Examiner—Humera N. Sheikh
(74) Attorney, Agent, or Firm—Bryan Cave LLP

(57) ABSTRACT

The invention is concerned with a novel process for the manufacture of flowable, non-dusty, binder-free riboflavin granulates by subjecting an aqueous suspension of riboflavin crystals of crystal modification B/C to a fluidized bed spray drying process, a single fluid nozzle spray drying process or a disk-type spray drying process.

16 Claims, No Drawings

PROCESS FOR PREPARING SPRAY GRANULES CONTAINING RIBOFLAVIN

FIELD OF THE INVENTION

The present invention is concerned with a novel process for the manufacture of flowable, non-dusty, and binder-free riboflavin granulates.

BACKGROUND OF THE INVENTION

Riboflavin granulates can be produced, for example, by a compacting process. European publication EP 0 414 115 BI describes a compacting process in which riboflavin powder with an average particle diameter smaller than 25 $\mu$m is pressed to strands. A comminution procedure follows the pressing operation to give riboflavin granulates having an average particle diameter of 50 $\mu$m to 1000 $\mu$m.

European publication EP 0 457 075 B1 describes a process for the production of flowable, non-dusty, and binder-free riboflavin granulates with a particle size of 50 $\mu$m to 450 $\mu$m from finely divided riboflavin. The process subjects an aqueous suspension or a suspension containing at least 10 wt. % water, which contains at least 5 to 30 wt. % of pure riboflavin, to a fluidized bed spray drying process that uses a single fluid nozzle spray drying process or a disk-type spray drying process at temperatures of 20 to 100° C. without adding a binder to the suspension. The riboflavin is produced by simply spray drying an aqueous suspension of riboflavin or by rapid precipitation from acidified, aqueous riboflavin solutions at temperatures below 50° C. or by rapid precipitation and rapid cooling of hot, aqueous riboflavin solutions at a pH value between 0.8 and 6.5. The crystal form of the riboflavin used is not disclosed. It is, however, generally known that the riboflavin production described in EP 0 457 075 B1 leads to riboflavin of crystal modification A.

A process for the production of dendritic riboflavin crystals is described in European Patent Application 98119686.8. This process involves pre-purification, crystallization, and drying. Needle-shaped riboflavin of stable modification A is dissolved in an aqueous mineral acid solution at about 30° C. and active charcoal is added to the resulting solution in order to adsorb impurities present in the solution. Thereafter, the medium containing the active charcoal is subjected to a cross-flow filtration over a ceramic membrane having a pore size of about 20 nm to about 200 nm. The five- to ten-fold amount (vol./vol.) of water is added to the resulting filtrate at about 30° C. The precipitated, spherical riboflavin crystals are separated by centrifugation or filtration.

If desired, the riboflavin crystals can be washed with water and subsequently dried according to methods known per se.

DETAILED DESCRIPTION OF THE INVENTION

The starting material used is needle-shaped riboflavin of modification A as is found, for example, in the production of foodstuffs. This riboflavin has a content of about 85 wt. % to about 98% of pure riboflavin. Varying amounts of chemical byproducts and/or fermentation residues, as well as water, are present depending on the route of production.

In the first stage of the process, needle-shaped riboflavin of modification A in dry or filter-moist form is dissolved in the aqueous mineral acid. The dissolution takes place by a protonation reaction. In the dissolution procedure, fermentation residues, such as proteins, peptides, amino acids, and/or chemical byproducts become liberated and are then present partly in solution and partly in solid form. As the mineral acid, there is especially suitable hydrochloric acid or nitric acid, the concentration of which is about 10 wt. % to about 65 wt. %. 18 wt. % to 24 wt. % hydrochloric acid is especially preferred. Up to about 19 wt. % dry riboflavin is dissolved in such an aqueous hydrochloric acid solution. The solution is thus almost saturated. The dissolution procedure is effected at temperatures up to a maximum of 30° C., usually at about 5 to about 25° C., preferably at about 10 to about 20° C., conveniently with intensive intermixing, for example by intensive stirring. The dissolution time can be reduced by increasing the temperature and/or intensifing the intermixing. The overall dissolution procedure usually takes up to about 30 minutes depending on the temperature and intermixing.

In the next stage of the process, active charcoal is added to the solution of the riboflavin in the aqueous mineral acid solution. Thereby, the impurities present in the solution are adsorbed on the active charcoal. The active charcoal can be pulverized or granulated. Conveniently, about 0.5 to about 9 wt. %, preferably about 3 wt. %, of active charcoal based on the riboflavin content is added. Depending on the impurities, the active charcoal is left in the solution for up to about 12 hours, preferably about 0.5 to about 3 hours. Acid-washed active charcoal with a bulk density of about 250 to about 400 kg/m$^3$, preferably about 300 kg/m$^3$, a specific surface area of about 1200 to about 1600 m$^2$/g, preferably about 1400 m$^2$/g, and an average particle size of about 20 to about 70 $\mu$m is suitable as the active charcoal. Examples of suitable active charcoals are Norit CA1 and Bentonorit, which are especially suitable for the adsorption biological impurities, as well as Norit SX 2, which in turn is especially suitable for the separation of chemical impurities.

In addition to the active charcoal there can be added to the aqueous mineral acid solution a filter aid, of which conveniently about 2 to about 9 wt. % based on the riboflavin content are used. Suitable filter aids are, for example, cellulose, such as Arbocel BWW 40 and B 800 from the company Rettenmaier & Söhne GmbH+Co.

The separation of the active charcoal, the filter aid, which may be present, and the undissolved fermentation residues present is effected by the subsequent cross-flow filtration. In addition to the adsorption, the active charcoal also has an abrasive action on the covering layer which forms the membrane. By this action, it is now possible to operate the membrane in a stable manner over a longer period of time with almost double the throughput than without active charcoal. The active charcoal thus possesses not only abrasive, but also adsorptive properties. The cross-flow filtration is effected over a ceramic membrane, which has a pore size of about 20 to about 200 nm, preferably of about 50 nm. The active charcoal pumped around in the circuit brings about by the abrasion a cleansing of the covering layer of carbon and fermentation residues formed on the membrane. As a rule, the counter-current velocity over the membrane is relatively high; it conveniently lies in the region of about 5 to about 6 m/s. In order not to compress the covering layer excessively, the trans-membrane pressure is conveniently1 to 2 bar (0.1 to 0.2 MPa).

After the cross-flow filtration, the solution of riboflavin, which is almost free from all impurities, the active charcoal, as well as filter aid, which may be present, is brought to crystallization, which is effected by the addition of a five- to ten-fold amount of water. The deprotonization of the riboflavin present in the aqueous mineral acid solution, which thereby takes place, leads to its precipitation.

The temperature of the medium in which the crystallization takes place can be varied in a range of 0 to 30° C. depending on the production method and impurity grade of the riboflavin. Especially in the case of synthetically produced material, the temperature can be increased to 30° C.; in the case of fermentative or relatively clean material temperatures below 10° C. are generally preferred. Most preferred is a temperature between 4 and 10° C. The crystallization can be carried out batchwise or continuously, preferably continuously. Cascades or individual kettles can be used as the crystallizer. Especially in the case of individual kettles, it is advisable to feed in at different positions in the kettle. Within the crystallizer, a very good macroscopic intermixing must be set up in every case. This can be realized, for example, by using a two-stage stirring device, with the feed solutions displaced by 180° being fed on to the upper and lower stirrer levels. Conveniently, in so doing, water is added to the upper level and the mineral acid solution of the riboflavin is added to the lower level. The stirring should be carried out very carefully in order not to damage the crystals. The residence time suitably varies between about 5 and about 20 minutes, preferably about 10–13 minutes. The subsequent filtration is effected using a filter or a centrifuge, which is very efficient. Preferably a band filter is used on which the washing may also be carried out. The drying can be carried out in a manner known per se.

The initial relative supersaturation in the crystallizer (prior to the addition of water) can be regulated by recycling the mother liquor as well as by water flowing into the crystallizer. The mother liquor:water ratio is conveniently about 1:1 to about 1:8. The relative supersaturation can be estimated via the conductivity present in the crystallizer, with a range of about 170 to about 200 mS/cm ideally being adhered to. The recycling of the mother liquor can be terminated depending on the conductivity. In the case of the recycling, it is preferably regulated via the conductivity existing in the crystallizer.

By a suitable choice of mixing ratio, temperature, and residence time, it is possible to crystallize an unstable modification of riboflavin, with the particles being spherical with a spiky surface and, thus, having a substantially larger surface area than the known needle-shaped crystals of modification A. The spherical crystal does not result by an agglomeration procedure as has hitherto been generally described in the literature for spherical crystals [see, for example, European Patent 0 307 767 B1 and Can. J. Chem. Eng. 47, 166–170 (1969)]; on the contrary, in the case of the new process, needle-shaped crystals grow from an initially crystallized-out, small, probably amorphous seed. The thus-obtained dendritic crystals correspond to the more soluble modifications B and, respectively, C, which have an adequate storage stability and, furthermore, by virtue of the unstable modification and larger surface area, have outstanding dissolution properties.

As mentioned above, the crystallizate is separated by filtration or centrifugation. The filter cake is washed with water. Subsequently, the moist filter cake can be dried.

The thus-produced dendritic crystals are a mixture of crystal modifications B and C, which are more unstable compared with modification A.

It has now surprisingly been found that flowable, non-dusty, and binder-free riboflavin granulates can be manufactured from a mixture of riboflavin crystals of modification B and C, which has been produced according to the process described above. The crystal modifications B and, respectively, C thereby do not revert back to the more thermostable needle-shaped crystal modification A.

The object of the invention is therefore a process for the manufacture of that flowable, non-dusty, and binder-free riboflavin granulates, which process comprises subjecting an aqueous suspension of riboflavin crystals of crystal modification B/C to a fluidized bed spray drying process, a single fluid nozzle spray drying process, or a disk-type spray drying process.

In the scope of the present invention the term "riboflavin crystals of crystal modification B/C" embraces riboflavin crystals as obtained according to the process described above. Dried crystals exhibit crystal modification B. In the moist state a mixture of crystals of modification B and C is present.

In the scope of the present invention the term "fluidized bed spray drying process", "single fluid nozzle spray drying process" or "disk-type spray drying process" embraces processes as described in European Patent EP 0 457 075 B1 and U.S. Pat. No. 5,300,303, respectively, which are herein incorporated by reference. The preferred drying process is a single fluid nozzle spray drying process.

The riboflavin is used in the form of an aqueous suspension. The suspension has a riboflavin content of about 5 wt. % to about 25 wt. %, preferably of about 9 wt. % to about 12 wt. %.

For the performance of the single fluid nozzle spray drying process, there is used a centrifugal-pressure nozzle as supplied, for example, by the company Schlick or by the company Spraying Systems. However, other centrifugal-pressure nozzles are also suitable.

The aqueous riboflavin suspension is sprayed into a drying tower by means of a centriftigal-pressure nozzle. The spraying pressure is up to 150 bar, preferably about 15 bar to about 40 bar.

The temperature of the drying gas is about 150° C. to about 240° C., preferably about 170° C. to about 200° C., at the entrance of the drying tower and about 70° C. to about 150° C., preferably about 80° C. to about 110° C., at the exit of the drying tower.

The riboflavin granulate obtained according to the process in accordance with the invention consists of particles with a particle size of about 20 μm to about 400 μm.

The surface structure of the spray-dried particles is spherical with folds and differs significantly from the surface structure of spray-dried particles from riboflavin of crystal modification A, which have a spherical smooth surface.

The spray granulate obtained according to the process in accordance with the invention surprisingly has the following advantages vis-à-vis the known riboflavin granulates of crystal modification A:

The riboflavin granulate has very good compression properties. The results will be evident from Tables 4 and 6.

Upon dissolution of the granulate in water, the riboflavin of crystal modification B shows a high solubility in comparison to riboflavin of crystal modification A. Solutions are obtained with a riboflavin concentration greater than 15 mg riboflavin/100 ml water, preferably greater than 16 mg riboflavin/100 ml water, more preferably about 16 mg riboflavin/100 ml water to about 18 mg riboflavin/100 ml water. When the granulate is dissolved in 0.1N HCl, solutions of about 18 mg riboflavin/100 ml 0.1N HCl to about 20 mg riboflavin/100 ml 0.1N HCl are obtained. The results are reproduced in Table 2.

Upon dissolution of a tablet that has been pressed from riboflavin granulates in accordance with the invention, a high solubility of the riboflavin of crystal modification B is observed. About 98 wt. % of the riboflavin has passed into solution after 45 minutes compared with 47 wt.% when using a riboflavin granulate from riboflavin of crystal modification A.

The riboflavin particles have a good mechanical stability, although no binder is added.

The riboflavin particles have a good chemical stability. The good stability remains even after storage at a high temperature.

EXAMPLES

The invention is illustrated on the basis of the following Examples:

Examples 1–3 relate to the production of a mixture of riboflavin crystals of crystal modification B and C.

Examples 4–6 describe riboflavin granulates in accordance with the invention.

Example 7 is a comparative Example.

Examples 8 and 9 describe the production of a tablet.

Example 1

The starting material used for the process described hereinafter was fermentatively produced riboflavin, which had a riboflavin content of 97.02% (according to HPLC), a residual moisture content ($H_2O$) of 0.80%, as well as an amino acid content of 1.11% and was present as needle-shaped crystals of the stable modification A.

350.0 g of this starting material were dissolved in 1708.6 g of 24% hydrochloric acid at 22° C. while stirring. After a dissolution period of about 15–20 minutes, a brown-black solution containing about 17% of riboflavin was present.

16 g (about 3% of the amount of riboflavin) of active charcoal (Norit® CA1) were subsequently added to the solution and the mixture was stirred for a further 4 hours. The mixture was filled into the double-jacketed feed tank of a laboratory membrane apparatus. The tank was cooled in order to maintain a maximum temperature of 35° C. Using a centrifugal pump the solution was pumped over a ceramic membrane with an effective surface area of 0.0055 $m^2$. The trans-membrane pressure was adjusted to 1.5 bar (0.15 MPa) and the cross-flow velocity over the membrane was adjusted to 6 m/s. This gave a permeate throughput of about 100 $l/m^2/h$, which could be maintained almost to the end of the filtration.

The hydrochloric acidic riboflavin solution was then crystallized in a continuously operating precipitation crystallizer.

The 3 l precipitation crystallizer was firstly filled with about 2 l of water and the liquid was stirred at 100 rpm with a two-stage inclined flat blade paddle stirrer and subsequently cooled to 10° C. Thereafter, at about 10° C., simultaneously and continuously, 1590 g/h of hydrochloric acidic riboflavin solution were dosed in at the upper stirrer and about 9000 g/h of water were dosed in at the lower stirrer. About 2–4 minutes after the start the riboflavin began to crystallize out as orange-yellow crystals. Initially, the separated crystals appeared to be flocculent, but after 20–30 minutes they changed into granular particles. The crystal suspension was then drained off continuously until in the crystallizer the 3 l mark (double jacket end) had been reached (i.e., after about 7 minutes). The valve was adjusted so that the level settled down at the 3 l mark. The discharged suspension was added directly to a P3 suction filter and there the solid was separated from the solution.

About 2500 ml of suspension were collected every 15 minutes and a filter cake about 1 cm thick was obtained. This was then washed in portions with 1300 ml of water until a pH of about 5 had been reached.

The moist, yellow crystallizate (65–75% residual moisture) was subsequently dried. Dried crystals exhibit crystal modification B.

Example 2

A riboflavin solution was produced and treated with active charcoal as described in Example 1. In contrast to Example 1, the solution was purified over a membrane having a pore size of about 50 nm. The trans-membrane pressure lay at 1.5 to 1.7 bar (0.15 to 0.17 MPa) and the cross-flow velocity lay at 5 to 6 m/s. This gave a permeate throughput of about 70 $l/m^2/h$. The crystallization, filtration and washing were carried out analogously to Example 1. The crystallization temperature lay between 9 and 10° C. and the drying was carried out in a laboratory drying oven at 100° C.

Dried crystals exhibit crystal modification B.

Example 3

The starting material used was chemically produced riboflavin having a content of 98%. The starting material was dissolved as described in Example 1. The cross-flow filtration was carried out as described in Example 2. The crystallization was carried out at 20° C. and by dosing in 1030 g/h of hydrochloric acidic riboflavin solution and 15060 g/h of water. Filtration and washing were carried out analogously to Example 2. The drying was carried out analogously to Example 2.

The results of the above three Examples are compiled in Table1 hereinafter. Dried crystals exhibit crystal modification B.

TABLE 1

| Example | Modification (according to X-ray structural analysis) | Riboflavin content according to HPLC | Lumichrome content according to HPLC | Lumiflavin content according to HPLC | Amino acid content |
|---|---|---|---|---|---|
| 1 | B | 98% | 0.08% | — | 0.1% |
| 2 | B | 98.9% | 0.15% | — | 0.06% |
| 3 | B | 99% | 0.15% | 0.25% | — |

The respective missing percentage number comprises the water content and other small impurities.

Example 4

The filter cake from Example 1 was diluted with water to give a suspension with a riboflavin content of 9.3 wt. %.

Example 5

The filter cake from Example 1 was diluted with water to give a suspension with a riboflavin content of 11.4 wt. %.

Example 6

The filter cake from Example 1 was diluted with water to give a suspension with a riboflavin content of 11.1 wt. %.

Example 7

Synthetically produced, commercial riboflavin of modification A was diluted with water to give a suspension with a riboflavin content of 32.0 wt. %. There were obtained very unstable particles which disintegrated to dust with low mechanical load and accordingly did not have the desired product properties.

The suspensions of Examples 4–7 were sprayed into a drying tower by means of a centrifugal-pressure nozzle. Table 2 hereinafter shows the process parameters and the improvement in the solubility of the riboflavin from the riboflavin granulates in accordance with the invention compared with known riboflavin granulate from riboflavin of crystal modification A.

TABLE 2

| Example | 4 | 5 | 6 | 7 |
|---|---|---|---|---|
| Crystal modification | B/C | B/C | B/C | A |
| Added amount of riboflavin suspension in kg/h | 56 | 41 | 56 | 103 |
| Dry substance of riboflavin suspension in % | 9.3 | 11.4 | 11.1 | 32.0 |
| Temperature of riboflavin suspension in ° C. | 22 | 27 | 22 | 14 |
| Spraying pressure in bar | 20 | 21 | 15 | 29 |
| Amount of drying air in kg/h | 2500 | 1670 | 1851 | 1797 |
| Air inlet temperature, ° C. | 180 | 165 | 200 | 190 |
| Air outlet temperature in ° C. | 115 | 97 | 106 | 110 |
| Riboflavin solubility in mg/100 ml water | 17.3 | 17.7 | 16.3 | 8.4 |
| Riboflavin solubility in mg/100 ml 0.1 N HCl | 19.2 | 19.6 | 18.4 | 10.1 |
| Riboflavin solubility in mg/100 ml water after storage for 9 months in a polyethylene bottle at 45° C./75% relative humidity | 17.7 | 17.7 | 15.6 | 9.2 |
| Riboflavin solubility in mg/100 ml 0.1 N HCl after storage for 9 months in a polyethylene bottle at 45° C./75% relative humidity | 18.9 | 18.4 | 18.1 | 10.0 |

Example 8

Tablets that contained about 100 mg of riboflavin were produced in a known manner according to the direct tabletting process. The suspensions described in Examples 4–7 were used. Table 3 hereinafter shows the composition of the tablets.

TABLE 3

| Riboflavin according to Example 4, 5 and 6 | 110 mg | |
|---|---|---|
| Riboflavin 98% tlc according to Example 7 | | 112.2 mg |
| Avicel pH 102 | 10.7 mg | 10.7 mg |
| Polyplasdone XL | 8.3 mg | 8.3 mg |
| Magnesium stearate | 1.0 mg | 1.0 mg |
| Total | 130.0 mg | 132.2 mg |

Table 4 hereinafter shows the improved compression properties of riboflavin granulates from riboflavin of crystal modification B vis-à-vis known riboflavin granulate from riboflavin of crystal modification A.

TABLE 4

| Riboflavin according to Example | 4 | 5 | 6 | 7 |
|---|---|---|---|---|
| Compression force | 700 kp | 700 kp | 700 kp | 700 kp |
| Hardness | 195 N | 191 N | 207 N | 159 N |

Example 9

Tablets that contained about 150 mg of riboflavin were produced in a known manner according to the direct tabletting process. The suspensions described in Examples 4–7 were used. Table 5 hereinafter shows the composition of the tablets.

TABLE 5

| Riboflavin according to Example 4, 5 and 6 | 165 mg | |
|---|---|---|
| Riboflavin 98% tlc according to Example 7 | | 168.4 mg |
| Avicel pH 102 | 11.0 mg | 11.2 mg |
| Polyplasdone XL | 3.0 mg | 3.07 mg |
| Magnesium stearate | 1.0 mg | 1.03 mg |
| Total | 180.0 mg | 183.7 mg |

Table 6 hereinafter shows the improved compression properties of riboflavin granulates 5 from riboflavin of crystal modification B vis-à-vis known riboflavin granulate from riboflavin of crystal modification A.

TABLE 6

| Riboflavin according to Example | 4 | 5 | 6 | 7 |
|---|---|---|---|---|
| Compression force | 500 kp | 500 kp | 500 kp | 500 kp |
| Hardness | 194 N | 207 N | 176 N | 76 N |
| Compression force | 800 kp | 800 kp | 800 kp | 800 kp |
| Hardness | 199 KN | 233 N | 225 N | 115 N |
| Compression force | 1000 kp | 1000 kp | 1000 kp | 1000 kp |
| Hardness | 254 N | 268 N | 244 N | 146 N |

The improved water solubility of riboflavin granulates from riboflavin of crystal modification B vis-à-vis known riboflavin granulate of crystal modification A can be determined in the "USP Dissolution Test." In the case of the product in accordance with the invention 98% to 100% of the riboflavin present in the tablets had dissolved after 45 minutes, while when tablets which contained riboflavin of crystal modification A were used only 47% of the riboflavin present in the tablets had dissolved.

While the invention has been illustrated and described with respect to illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

What is claimed is:

1. A process for the manufacture of flowable, non-dusty, and binder-free riboflavin granulates, which process comprises drying an aqueous riboflavin crystal suspension of crystal modification B/C by a process selected from the group consisting of a fluidized bed spray drying process, a single fluid nozzle spray drying process, and a disk-type spray drying process.

2. A process in accordance with claim 1, wherein the drying process is a fluidized bed spray drying process.

3. A process in accordance with claim 1, wherein the drying process is a single fluid nozzle spray drying process.

4. A process in accordance with claim 1, wherein the drying process is a disk-type spray drying process.

5. A process in accordance with claim 1, wherein the aqueous suspension has a riboflavin content of about 5 wt. % to about 25 wt. %.

6. A process in accordance with claim 5, wherein the riboflavin content is about 9 wt. % to about 12 wt. %.

7. A process in accordance with claim 1, wherein a centrifugal-pressure nozzle sprays the aqueous suspension into a drying tower at a spray pressure up to 150 bar.

8. A process in accordance with claim 7, wherein the spray pressure is about 15 bar to about 40 bar.

9. A process in accordance with claim 7, wherein the drying gas temperature at the entrance of the drying tower is about 150° C. to about 240° C.

10. A process in accordance with claim 9, wherein the temperature is about 170° C. to about 200° C.

11. A process in accordance with claim 7, wherein the drying gas temperature at the exit of the drying tower is about 70° C. to about 150° C.

12. A process in accordance with claim 11, wherein the temperature is about 80° C. to about 110° C.

13. A riboflavin granulate obtained by a process in accordance with claim 1.

14. A riboflavin granulate in accordance with claim 13, having particles with a particle size of about 20 $\mu$m to about 400 $\mu$m.

15. A process for producing an aqueous riboflavin solution comprising dissolving a riboflavin granulate of claim 13 in water to form a solution having a riboflavin concentration greater than 16 mg riboflavin/100 ml water.

16. A process for the production of tablets from a riboflavin granulate in accordance with claim 13, which process comprises pressing the riboflavin granulate at a compression pressure of about 500 kp to about 1000 kp.

* * * * *